United States Patent [19]

Ishiguro et al.

[11] Patent Number: 5,211,176

[45] Date of Patent: May 18, 1993

[54] ULTRASOUND EXAMINATION SYSTEM

[75] Inventors: Masaaki Ishiguro; Toshizumi Tanaka; Yukio Takagi, all of Omiya, Japan

[73] Assignee: Fuji Photo Optical Co., Ltd., Omiya, Japan

[21] Appl. No.: 800,437

[22] Filed: Nov. 29, 1991

[30] Foreign Application Priority Data

Nov. 30, 1990 [JP] Japan .................................. 2-329997

[51] Int. Cl.$^5$ ............................................. A61B 10/00
[52] U.S. Cl. ............................ 128/662.06; 128/662.03; 128/660.09
[58] Field of Search ...................... 128/662.06, 660.09, 128/660.08, 662.03, 662.05

[56] References Cited

U.S. PATENT DOCUMENTS

| | | | |
|---|---|---|---|
| 4,637,256 | 1/1987 | Sugiyama et al. | 128/660.09 |
| 4,756,313 | 1/1988 | Terwilliger | 128/662.06 |
| 4,817,616 | 4/1989 | Goldstein | 128/662.06 |
| 5,050,610 | 9/1991 | Oaks et al. | 128/662.06 |
| 5,054,492 | 10/1991 | Scribner et al. | 128/662.06 |

*Primary Examiner*—Kyle L. Howell
*Assistant Examiner*—George Manuel
*Attorney, Agent, or Firm*—Oblon, Spivak, McClelland, Maier & Neustadt

[57] ABSTRACT

An ultrasound examination system, including an ultrasound probe detachably connected at its proximal end to a probe operating unit and having an ultrasound transducer rotatably mounted on the tip end of a flexible insert member and a rotation transmitting means passed through the insert member to rotate the ultrasound transducer. The probe operating unit is provided with a linear operating means for displacing the ultrasound transducer linearly for a linear scan, and a radial operating unit for rotating the ultrasound transducer for a radial scan, in combination with a mode selector means for switching the operation of the ultrasound transducer between linear scan mode in which the transducer is displaced linearly during transmission and reception of ultrasound signals and a radial scan mode in which the transducer is rotated during transmission and reception of ultrasound signals.

10 Claims, 13 Drawing Sheets

FIG. 1
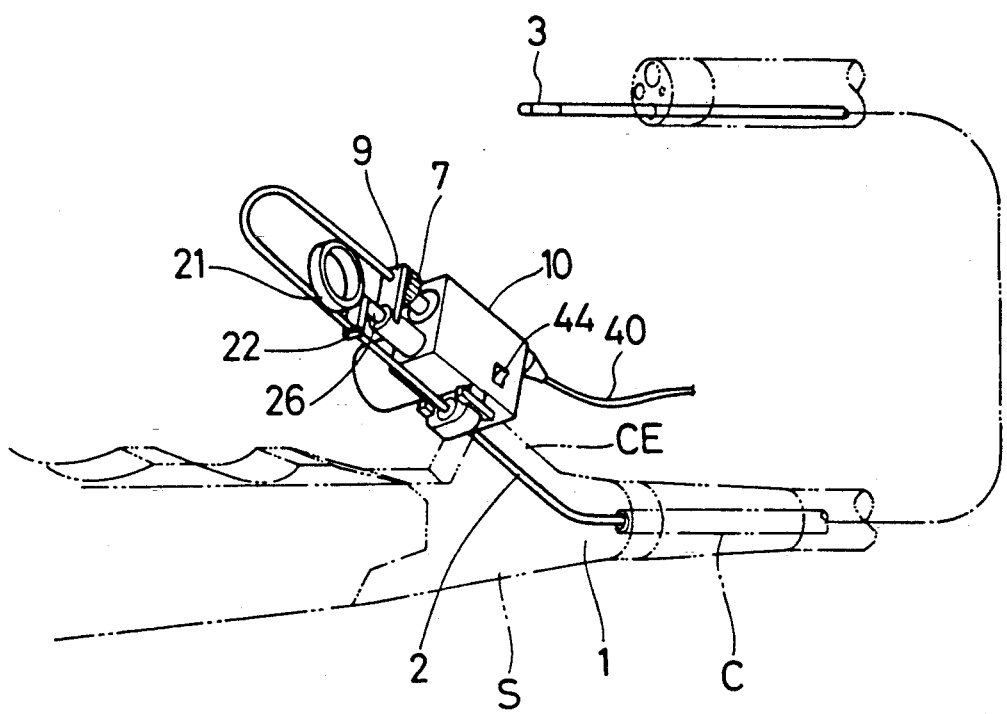
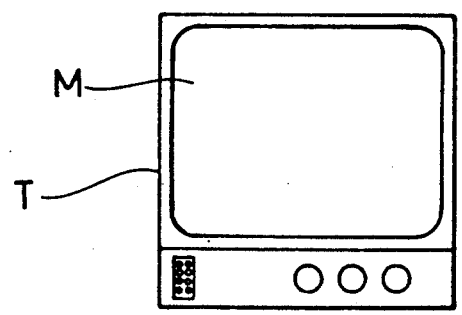

F I G. 4
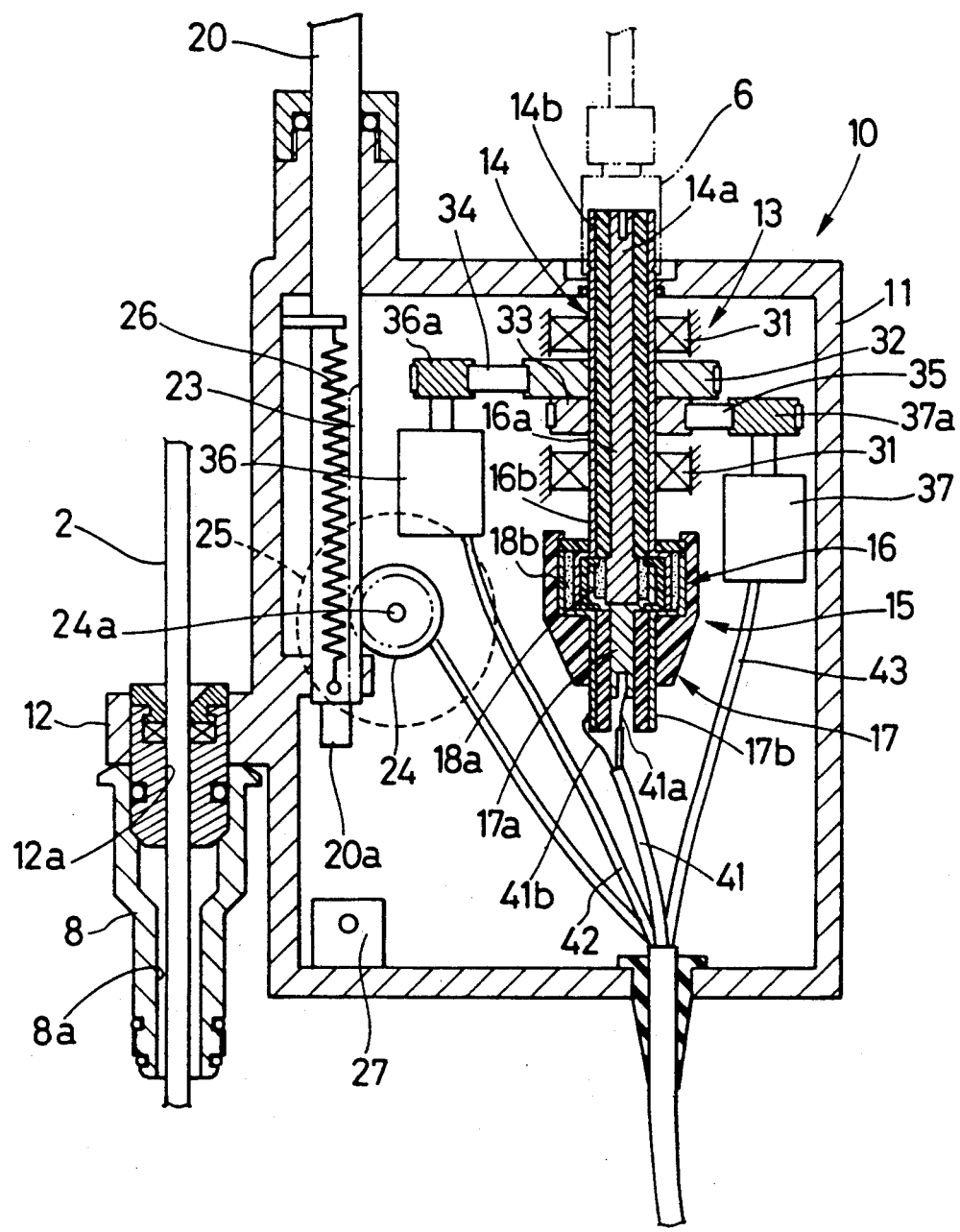

ULTRASOUND EXAMINATION SYSTEM

BACKGROUND OF THE INVENTION

1. Field of the Invention

This invention relates to an ultrasound examination system employing an ultrasound probe to be inserted into an intracavitary portion of human body or the like for ultrasound diagnosis or examination.

2. Description of the Related Art

Ultrasound examination systems are widely used in medical fields, and are usually composed of an ultrasound probe with an ultrasound vibratory element or transducer and an ultrasound image observation terminal which is largely constituted by circuits for transmission and reception of ultrasound signals, circuits for processing ultrasound echo signals and an ultrasound image monitor. Ultrasound energy is transmitted into a body and its echo signals are received by the ultrasound transducer. The received echo signals are transferred to the signal processing circuits of the observation terminal to obtain ultrasonically imaged information, for example, on the condition of intracorporeal tissues and display it on a monitor as an ultrasound image.

In this connection, for ultrasound examination or diagnosis, it is desirable to insert an ultrasound transducer to a position proximal to an intracavitary wall portion of interest and to transmit and receive ultrasound energy at that position for the purpose of enhancing the accuracy and functions of the ultrasound examination or diagnosis, as disclosed in U.S. Pat. No. 4,802,487. For three-dimensional examination, there has been known an ultrasound probe which is adapted to be inserted into a patient's body through a biopsy channel usually provided on an endoscope for insertion of forceps or other biopsy instruments, thereby obtaining ultrasonically imaged information on the tissues of an intracavitary wall portion of interest in addition to endoscopic examination and diagnosis.

For obtaining ultrasound images, it has been the general practice to scan the ultrasound transducer either by an electronic or mechanical scan system. Existing mechanical scan systems include a linear type in which an ultrasound transducer is displaced linearly, and a radial type in which an ultrasound transducer is turned about an axis of rotation. In this regard, from the standpoint of reducing the size of the ultrasound element into a compact form, the mechanical scan system is usually resorted to in case of ultrasound probes of the type which is designed to be inserted into an intracavitary portion of interest through a biopsy channel of an endoscope as mentioned above.

In a system of the mechanical linear scan type, an ultrasound transducer which is mounted at the tip end of an ultrasound probe is inserted into the body in such a way as to contact an intracavitary wall portion or other portion of interest or to face such an intracavitary wall portion through ultrasound transmissive material like water, and the ultrasound probe is pushed forward or backward manually or by the use of a suitable drive means like an electric motor. As the ultrasound transducer is displaced linearly, ultrasound energy is directed into the intracavitary wall portion while receiving return echoes through the ultrasound transducer, and the extent of its displacement is detected by an encoder or other suitable position sensor means to produce position signals according to which an ultrasound image is displayed on a monitor. On the other hand, in an ultrasound examination system of the mechanical radial scan type, the ultrasound probe is connected to a rotational drive means like an electric motor and thereby put in rotation during transmission and reception of ultrasound signals. The scan system of this type is provided with a sensor means to detect the rotational angle of the ultrasound transducer, thereby obtaining position signals for display of ultrasound images.

Of these two types of scanning, either the linear or radial scan is more advantageous depending upon the locality and nature of the ultrasound examination. However, conventional mechanical scan type ultrasound probes are constructed exclusively for either a linear or radial scan mode, without permitting to change the scan mode arbitrarily whenever a necessity arises during examination.

SUMMARY OF THE INVENTION

In view of the foregoing situations, it is an object of the present invention to provide an ultrasound probe which permits the operator to select either a linear or radial scan mode according to the nature of examination.

It is another object of the present invention to provide an ultrasound probe to be manipulated under eye observation through an endoscope, the probe permitting the operator to get ultrasound images of intracavitary walls or intracorporeal tract walls in both transverse and longitudinal sections easily by switching the mode of operation.

In accordance with the present invention, there is provided, for achieving the above-stated objectives, an ultrasound examination system which essentially includes: an ultrasound probe having an ultrasound transducer rotatably mounted on a tip end portion of a flexible insert member and a rotation transmitting means fitted in the insert member to transmit rotation to the ultrasound transducer; a probe operating unit including a linear operating means detachably connected to a base end portion of the ultrasound transducer to move the same linearly along the axis of the tip end portion of the insert member for a linear scan, and a radial operating means coupled with the ultrasound transducer to turn same about the axis of the tip end portion for a radial scan; and a scan mode selector means for switching the operation of the ultrasound transducer from linear scan mode to radial scan mode or vice versa.

BRIEF DESCRIPTION OF THE DRAWINGS

The above and other objects, features and advantages of the invention will become apparent from the following description of preferred embodiments and the appended claims, taken in conjunction with the accompanying drawings which are given only for illustrative purposes and not for restrictive purposes in any way whatsoever. In the accompanying drawings:

FIGS. 1 through 5 illustrate a first embodiment of the invention, of which:

FIG. 1 is a schematic view of an ultrasound examination system, showing its general arrangement;

FIG. 2 is a schematic sectional view of an insert member;

FIG. 3 is a schematic outer view of a probe operating unit;

FIG. 4 is a schematic sectional view of the operating unit; and

FIG. 5 is a block diagram showing the general arrangement of a scan mode selector mechanism;

FIGS. 6 through 15 illustrate a second embodiment of the invention, of which:

FIG. 6 is a schematic outer view of an operating unit;

FIG. 7 is a schematic sectional view of the operating unit of FIG. 6;

FIG. 8 is a sectional view taken on line X—X of FIG. 7;

FIG. 9 is a schematic perspective view of a probe gripper member;

FIG. 10 is a schematic view of the probe member, explanatory of its operation;

FIG. 11 is a schematic sectional view of a finger ring;

FIG. 12 is an exploded perspective view of the finger ring of FIG. 11;

FIG. 13 is a schematic view of a cover member, explanatory of its operation;

FIG. 14 is an outer view of the cover member concealing a rotating member thereunder; and FIG. 15 is a schematic view of a positioning mechanism for the cover member.

DESCRIPTION OF PREFERRED EMBODIMENTS

Figure 2:
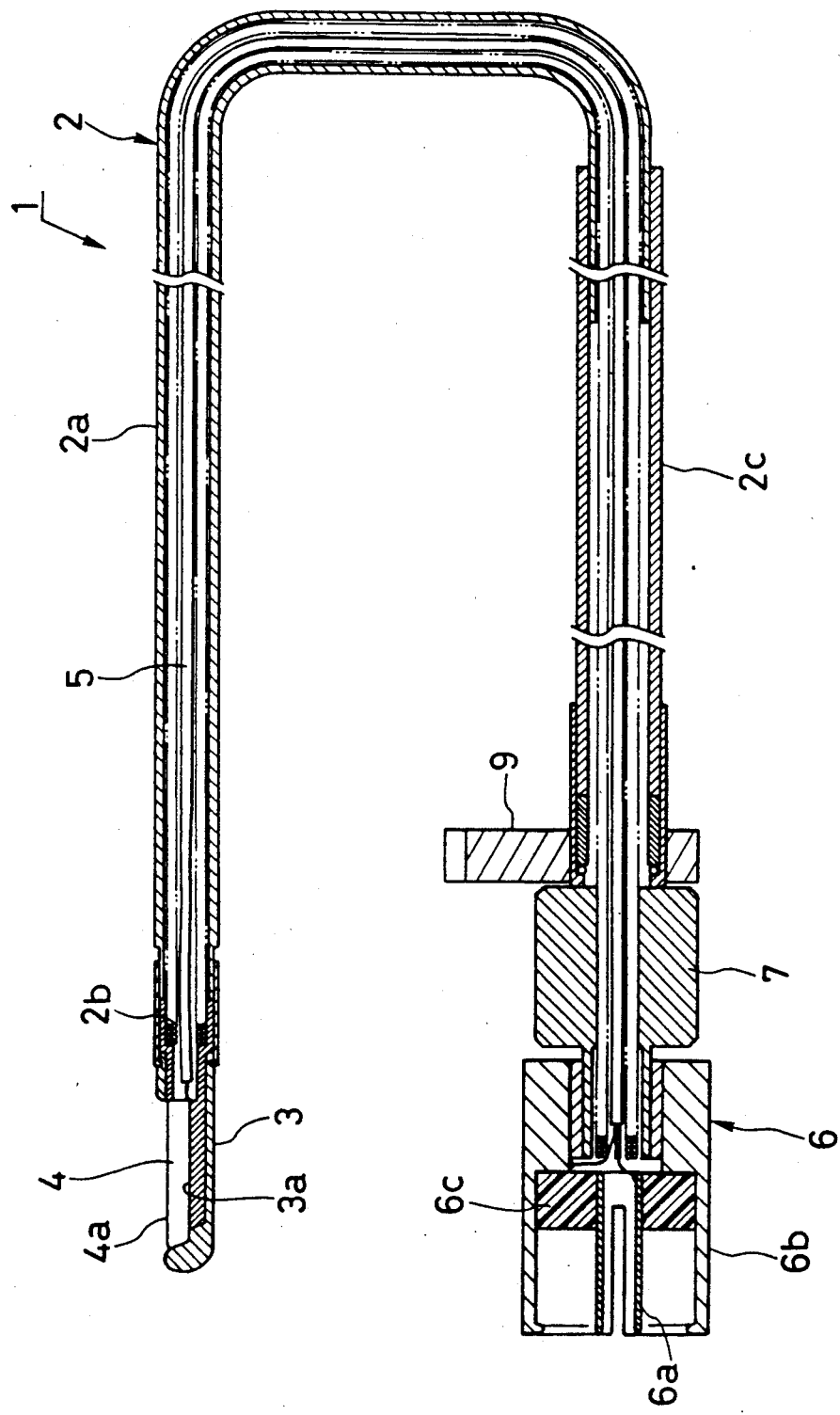

Hereafter, the invention is described more particularly by way of the preferred embodiments shown in the drawings.

In the following description, the invention is embodied into an endoscopic ultrasound probe which is adapted to be inserted to position of interest through a biopsy channel C which is provided on an endoscope S for insertion of forceps or other instruments. However, needless to say, the invention can be applied to other ultrasound probes which are designed to be directly inserted into human body.

Shown in FIG. 1 is the general arrangement of an ultrasound examination system, wherein the reference 1 denotes an ultrasound probe which has a hollow rigid tip member 3 fixed to the tip end of a flexible insert member 2. A single-element ultrasound transducer 4 is fitted in a cavity 3a in the tip member 3. The tip member 3 is rotatable relative to the insert member 2, and, for transmission and reception of signals, the ultrasound transducer 4 on the tip member 3 has an active surface 4a directed toward an opening which is formed at one side of the rigid tip member 3. The ultrasound transducer 4 is scanned in a linear or radial direction to obtain a cross-sectional ultrasound image, for example, of intracavitary wall tissues within the scan range.

The insert member 2, to be inserted through the biopsy channel C of the endoscope S, is in the form of a control cable of a small diameter suitable for insertion into the biopsy channel, having as shown particularly in FIG. 2, a rotation transmitting flexible shaft 2b fitted in a flexible sleeve 2a of a soft low-friction material like a fluorine resin, the flexible transmission shaft 2b consisting of at least a couple of coils of fine metal wires which are tightly wound in such a manner as to form a single layer of parallelly coextensive helices or to form radially overlapped layers of helices. The insert member 2 has a function of rotating the ultrasound transducer 4 on the rigid tip member 2 by remote control. A coaxial cable including ultrasound signal transmission and reception lines 5 is fitted in the flexible rotation transmitting shaft 2b. The fore ends of the coil springs of the flexible transmission shaft 2b are fixed to the rigid tip member 3 thereby to transmit the torque of rotational operation to the ultrasound transducer 4. When rotating the ultrasound transducer 4, the signal transmission/reception cable 5 is also turned together with the flexible transmission shaft 2b.

A connector 6 which is formed at the terminal end of the ultrasound probe 1 is disconnectibly connectible to a probe operating unit 10 which is manipulated by the operator for scanning the ultrasound probe 1. The connector 6 is constituted by an electrode pin 6a to which a line 5a of the signal transmission/reception cable is connected, and a split cylindrical socket 6b to which a line 5b of the transmission/reception cable 5 is connected. The cylindrical socket 6b is formed of a conducting material and insulated from the electrode pin 6a by an insulating member 6 which is inserted therebetween. The socket 6b is connected to a rotating member 7 which is fixedly fitted on the base end of the flexible transmission shaft 2b. The rotating member 7 is manually operated to turn the flexible transmission shaft 2b when turning the active surface 4a of the ultrasound transducer 4 into a desired radial direction. The sleeve portion 2a of the insert member 4, to be led out of the proximal end of the biopsy channel C of the endoscope S, is covered with a protective sleeve 2c which has higher rigidity than the sleeve 2a. In FIG. 2, the reference 9 denotes a stopper plate which blocks rotation of the protective sleeve 2c.

Figure 3:
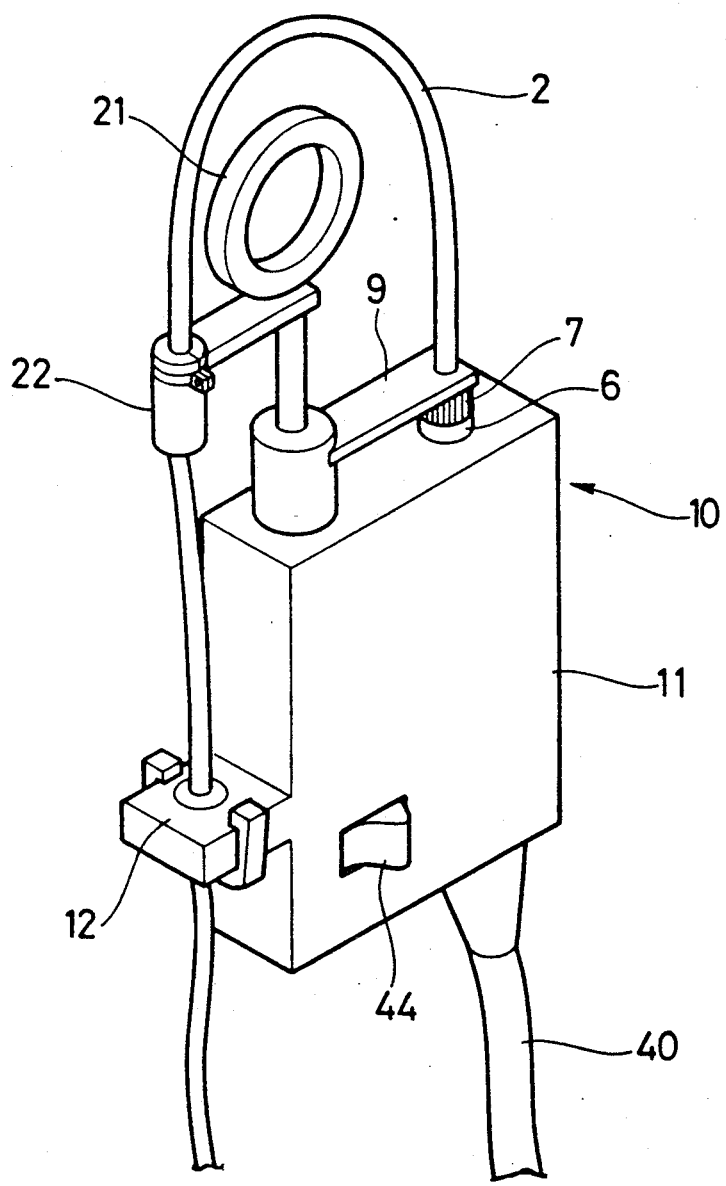

As seen in FIGS. 3 and 4, the probe operating unit 10 is provided with, within its casing 11, a linear operating means for displacing the ultrasound transducer 4 linearly in the axial direction of the rigid tip member 3 and a radial operating means for turning the ultrasound transducer 4 about the axis of the rigid tip member 3 to get ultrasonically imaged information in radial directions.

As clear from FIG. 1, the operating unit 10 is adapted to be detachably mounted at the proximal end CE of the biopsy channel C on the endoscope S. To this end, the casing 11 of the operating unit 10 is contiguously provided with a mount member 12 with a mount piece 8 which is detachably connectible to the proximal end CE of the biopsy channel C when the ultrasound probe 1 is mounted thereon. The mount piece 8 has a function as an adaptor for connecting the operating unit 10 to endoscopes of different types. The mount piece 8 and mount member 12 are provided with through holes 8a and 12a, respectively, to receive the insert member 2 of the ultrasound probe 1. The connector 6 at the terminal end of the insert member 2 of the ultrasound probe 1, which is led through the holes 8a and 12a in the mount piece 8 and mount member 12, is detachably connected to a rotational mechanism 13 within the casing 11.

The rotational mechanism 13 is constituted by a rotary member 14 and a rotary connector 15. The rotary connector 15 is constituted by a rotary part 16 which is formed integrally with the rotary member 14, and a fixed part 17. One end of the rotary member 14 is slightly protruded from of the casing 11 for fitting engagement with the connector 6 on the insert member 2. The rotary part 16 and fixed part 17 of the rotary connector 15 are provided with a pair of electrodes 16a and 16b and a pair of electrodes 17a and 17b, respectively. The electrodes 16a and 16b are electrically connected with the electrodes 17a and 17b, respectively, through fluid contacts 18a and 18b using mercury or other conductive fluid. An insulating member 19 is inserted between the electrodes 16a and 16b and between the electrodes 17a and 17b. The electrodes 16a and 16b of the rotary part 16 are connected to terminals 14a and 14b at the fore end of the rotary member 14, and, when the connector 6 of the ultrasound probe 1 is fitted on the rotary member 14, the electrode pin 6a and the cylindrical socket 6b of the connector 6 are connected to the terminals 14a and 14b, respectively. On the other hand, the fixed part 17 is connected with a signal transfer line 41 of a flexible cable 40 which is connected to the ultrasound image observation terminal T. More specifically, the fixed part 17 of the rotary connector 15 is provided with electrodes 17a and 17b which are insulated from each other by an interposed insulating member and connected to wires 41a and 41b of the signal transfer line 41, respectively.

The operating unit 10 is provided with linear and radial operating means to provide linear and radial scan modes for the ultrasound transducer 4.

The linear operating means is provided to scan the ultrasound transducer 4 linearly in the axial direction of the rigid tip member 3 over a predetermined range by pulling the insert member 2 back and forth. For this purpose, an operating rod 20 is axially slidably mounted on the casing 11. The operating rod 20 is provided with a finger holder ring 21 at its outer end which is led out of the casing 11, along with a probe gripper member 22 which is adapted to releasably grip a proximal end portion of the insert member 2 which is covered with the protective sleeve 2c and passed through the holes 8a and 12a in the mount piece 8 and mount member 12. The proximal end portion of the insert member 2 behind the probe gripper member 22 is arcuately looped over a predetermined length toward its rear end terminating with the connector 6 which is detachably connected to the operating unit 10. When connected to the probe gripper member 22, the insert member 2 is fixed thereto to prevent its positional deviations in the axial and rotational directions. As the operating rod 20 is pulled back and forth in the axial direction by the operator putting a finger in the finger holder ring 21, the rigid tip member 3 is moved axially together with the insert member 2 through the probe gripper member 22, displacing the ultrasound transducer 4 on the tip member 3 axially for linear scan.

While the ultrasound transducer 4 is being operated in this manner, the received return signals are transmitted to the ultrasound observation terminal T to display an ultrasound image on the monitor M. In doing so, it is necessary to obtain a signal indicative of the axial position of the ultrasound transducer 4 in addition to the signal of return echoes picked up by the transducer 4. For this purpose, a rack 23 is formed on the operating rod 20, which is received in the casing 11, and meshed with a pinion 24 on a pinion shaft 24a which is connected to an encoder 25. Consequently, the position of the operating rod 20 is detected from the output signal of the encoder 25.

The operating rod 20 is constantly urged to project outward of the casing 11 under the influence of a return spring 26. When the operating rod 20 is once pushed into the casing 20 against the action of the return spring 26 and then operated in the outwardly protruding direction, the ultrasound transducer 4 at the tip end of the insert member 2 is moved over a certain range in a retracting direction toward the endoscope S to make a scan of that range. Further provided within the casing 11 is an optical sensor 27 which serves to detect the end position of the inward stroke of the operating rod 20, in cooperation with a light blocking plate 20a which is provided contiguously at the inner end of the operating rod 20. A position where the light blocking plate 20a is detected by the optical sensor 27 is used as a reference position for an axis along which an ultrasound image is displayed on the monitor M of the ultrasound image observation terminal T. The reference position signal from the optical sensor 27 is transmitted to the observation terminal T along with the output signal of the encoder 25.

Turning now to the radial operating means, it is arranged to rotationally drive the rotary member 14 together with the cylindrical socket member 6b of the connector 6 which is in fitting engagement with the rotary member 14, thereby torsionally turning the rotation transmitting flexible shaft 2b and rotationally driving the rigid tip member 3 to turn the ultrasound transducer 4 about the axis thereof. To this end, the rotary member 14 is rotatably supported by bearings 31 within the casing 11, and provided with a couple of pulleys 32 and 33 which are connected to a pulley 36a of a rotational drive motor 36 and a pulley 37a of an encoder 37 through belts 34 and 35, respectively. Wires 42 and 43 from the motor 36 and encoder 37 are connected to the ultrasound image observation terminal T through the flexible cable 40.

Thus, upon actuating the motor 6, the ultrasound transducer 4 is rotationally driven to turn about the axis of the rigid tip member 3. Simultaneously, ultrasound pulses are directed into an intracavitary wall portion, while receiving return echoes to form an ultrasound image in the radial direction on the basis of the output signal of the encoder 37 indicative of the rotational angle of the ultrasound transducer 4.

In a radial scan, the signal transmission/reception line 5 is turned along with the rotation of the ultrasound transducer 4, not to mention the flexible transmission shaft 2b. On the other hand, the signal transfer line 41 which is electrically connected with the transmission/reception line 5 should not be rotated, because it is assembled into the cable 40 leading to the observation terminal T. Therefore, the signal transmission/reception line 5 is connected to the signal transfer line 41 not directly but through a relay means which is constituted by the rotary member 14 and rotary connector 15. It follows that the torque resulting from the rotating operation of the ultrasound transducer 4 is transmitted up to the rotary part 16 of the rotary connector 15 but not to the fixed part 17. Besides, since the rotary and fixed parts 16 and 17 are electrically connected through the fluid contacts 18a and 18b, there is no possibility of the rotary part 16 producing scratching noises or causing signal attenuation as a result of its rotation. Further, for adjustment of the position or angle of the ultrasound transducer 4, a necessity for turning the flexible transmission shaft 2b through manipulation of the rotating member 7 arises not only in a radial scan operation but also in a linear scan operation. Even in such a case, the intervening rotary connector 15 suitably prevents twisting of the cable 40 which might impair the positioning accuracy of the ultrasound transducer 4.

As mentioned hereinbefore, the ultrasound examination system is switchable between a linear scan mode in which the ultrasound transducer 4 is displaced linearly in the axial direction by manipulating the linear operating means, and a radial scan mode in which the ultrasound transducer 4 is turned about the axis of the rigid tip member 3 by manipulating the radial operating means. For switching the scan mode, a selector switch 44 which serves as the afore-mentioned mode selector means is mounted on a side wall of the casing 11, permitting the operator to switch the operation from the linear scan mode to the radial scan mode or vice versa.

Figure 5:
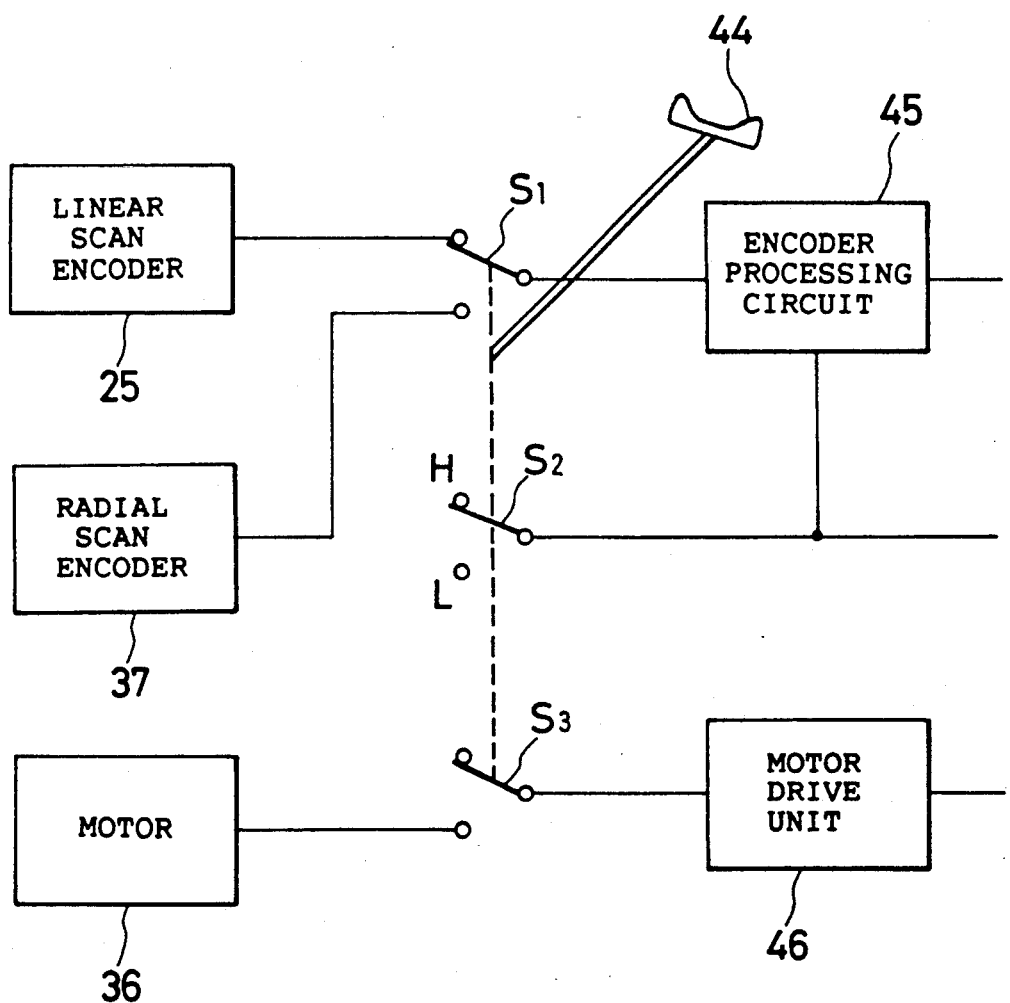

More specifically, as shown in FIG. 5, either the linear scan encoder 25 or the radial scan encoder 37 is connected to an input terminal of an encoder processing circuit 45 through a switch S1. The other terminal of the encoder processing circuit 45 is connected to either a high voltage terminal H or a low voltage terminal L through a switch S2. The motor 36 is connectible to a motor drive unit 46 through a switch S3. In this instance, the switches S1 to S3 are operated by a common selector switch 44 in an interlocked fashion. Namely, as the selector switch 44 is turned to one side, the linear scan encoder 25 is connected to the encoder processing circuit 45, and simultaneously the other terminal of the encoder processing circuit 45 is connected to the terminal H to put the encoder 25 in operable state. At this time, the motor 36 is disconnected from the motor drive unit 46. When the selector switch 44 is turned to the other side, the radial scan encoder 37 is connected to the encoder processing circuit 45, and simultaneously the other terminal of the encoder processing circuit 45 is connected to the terminal L to put the encoder 37 in operable state. At the same time, the motor 36 is put in operable state by connection with the motor drive unit 46.

The ultrasound probe operating mechanism of this embodiment operates in the manner as follows.

Firstly, the endoscope S is inserted into a patient's body until its fore end reaches a locality of examination or diagnosis, and then the insert member 2 of the ultrasound probe 1 is introduced into the biopsy channel C of the endoscope S, protruding the rigid tip member 3 from the fore end of the endoscope S over a predetermined length. Nextly, the mount member 12 which is contiguously provided on the casing 11 of the probe operating unit 10 is fixed to the proximal end CE of the biopsy channel C through the mount piece 8, while fixing a proximal end portion of the insert member 2 to the probe gripper member 22 and coupling the connector 6 with the rotational mechanism 13 on the operating unit 10. Now, the ultrasound probe 1 can be put in either linear scan mode or radial scan mode.

If the linear scan mode is chosen through the mode selector switch 44, a linear scan can be made by manipulating the finger grip 21 on the operating rod 20 with a finger or fingers. For a linear scan, for example, the operating rod 20 is pushed into the casing 11 of the operating unit 10 and then moved outward. By this action, the ultrasound probe 1 is pulled in the retracting direction toward the biopsy channel C of the endoscope, moving the ultrasound transducer 4 linearly over a certain scan range. During the linear movement, ultrasound pulses are directed, for example, to an intracavitary wall portion of interest and return echoes are received by the ultrasound transducer 4 alternately at predetermined time intervals according to the output signal of the encoder 25 indicative of the linear or axial position of the ultrasound transducer 4, transmitting the received return echoes to the ultrasound image observation terminal T. At the same time, the position signal from the encoder 25 is sent to the ultrasound image observation terminal T as a reference signal in setting the image display position on the monitor M. These signals are processed in a signal processing section of the observation terminal T to form an ultrasound image of intracavitary wall tissues or other part to be displayed on the monitor M for examination or diagnostic purposes. Since the insert member 2 is looped in its proximal end portion between the probe gripper member 22 of the operating unit 10 and its terminal end connected to the rotational mechanism 13, it always contains an extra margin to permit the operator to pull the insert member 2 back and forth without imposing a pulling force on the connection to the rotational mechanism 13 during the scanning operation and to absorb the difference in length between the insert member 2 and the insert portion of the endoscope S.

On the other hand, when the radial scan mode is selected, the motor 36 in the operating unit 10 is actuated to rotate the rotary member 14, and the rotation of the rotary member 14 is transmitted to the flexible transmission shaft 2b in the insert member 2 through the connector 6, turning the ultrasound transducer 4 on the rigid tip member 3 at the fore end of the flexible transmission shaft 2b about the axis of the rigid tip member 3. During this rotation, ultrasound pulses are directed, for example, into an intracavitary wall portion of interest and return echoes are received by the ultrasound transducer 4 alternately at predetermined time intervals according to the angular position signal from the encoder 37. Since the encoder 37 is rotationally driven during rotation of the rotary member 14, its output signal is supplied to the ultrasound image observation terminal T. Thus, a radial ultrasound image can be generated on the basis of the received ultrasound echo signals and the angular position signals from the encoder 37. The rotation of the rotary member 14 is transmitted up to the rotary part 16 of the rotary connector 15 but never transmitted to the fixed part 17 which is connected with the rotary part 16 through the fluid contacts 18a and 18b.

Referring now to FIGS. 6 through 15, there is shown a second embodiment of the invention. In this embodiment, the construction of the ultrasound probe 1 is same as in the above-described first embodiment, except that a manually operable rotating member is not provided on a terminal connector of the probe to be coupled with the rotary connector on the probe operating unit 10. Therefore, in the following description, the same reference numerals are employed for the respective component parts except the terminal connector of the insert member 2, which is designated by a reference numeral 6'. This embodiment can also change the mode of operation from the linear to radial scan mode or vice versa.

Figure 6:
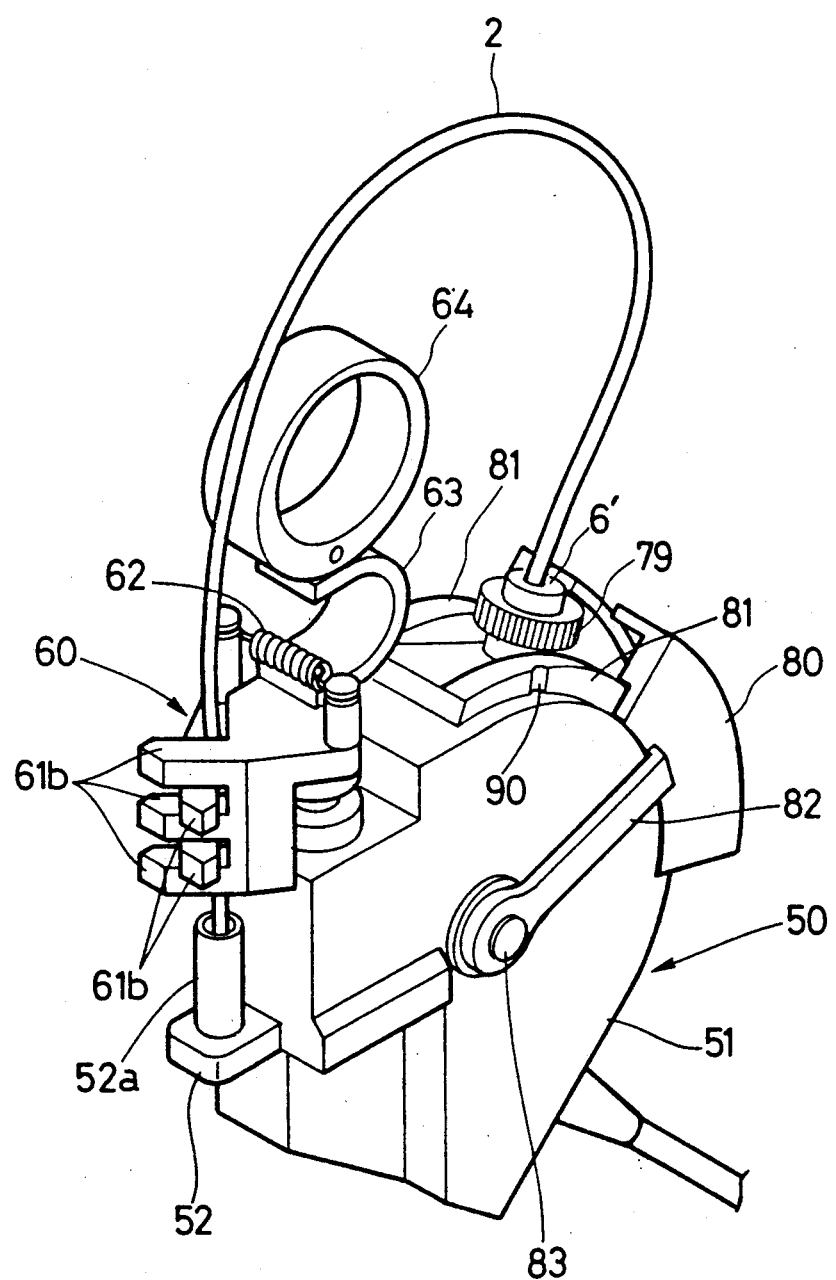
Figure 7:
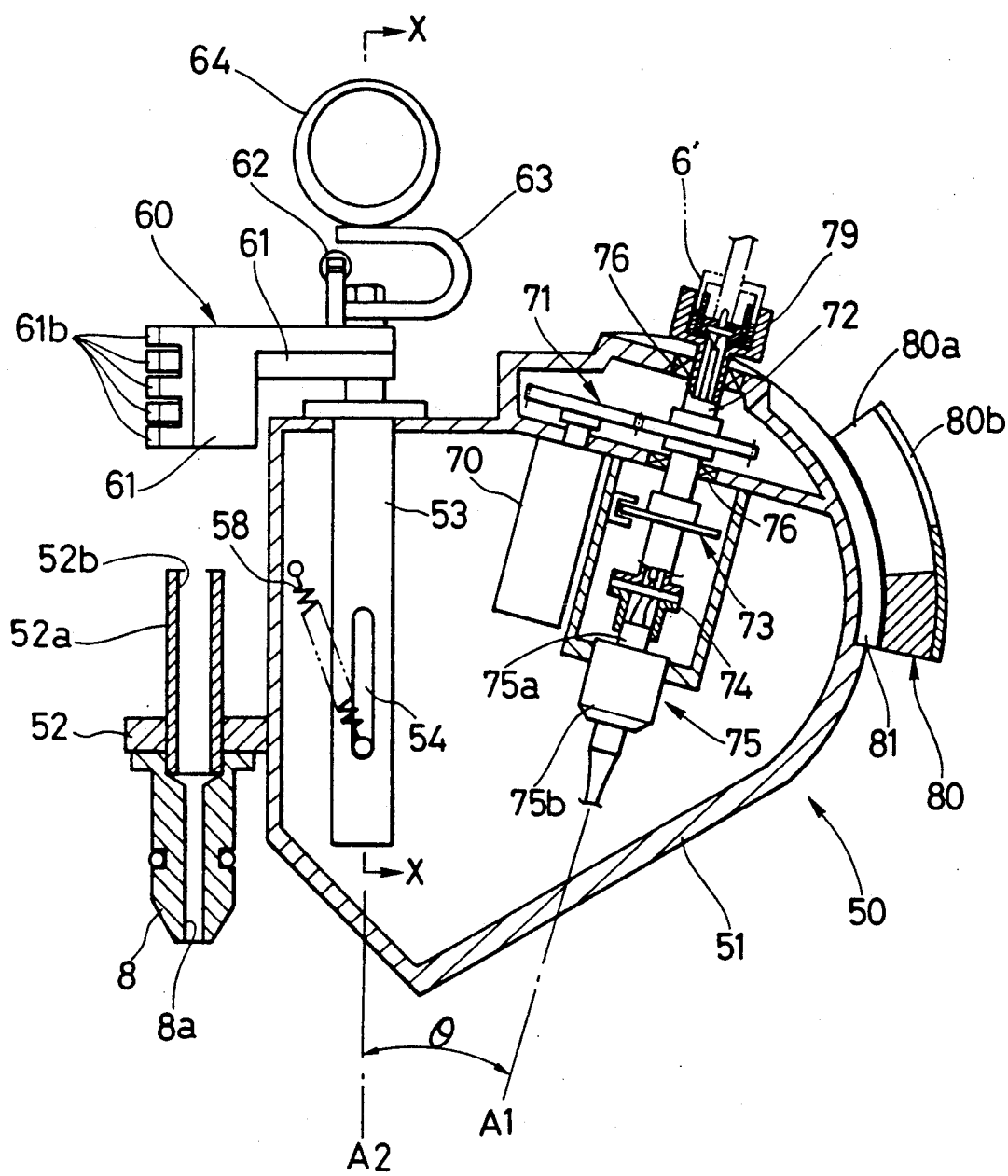
Figure 8:
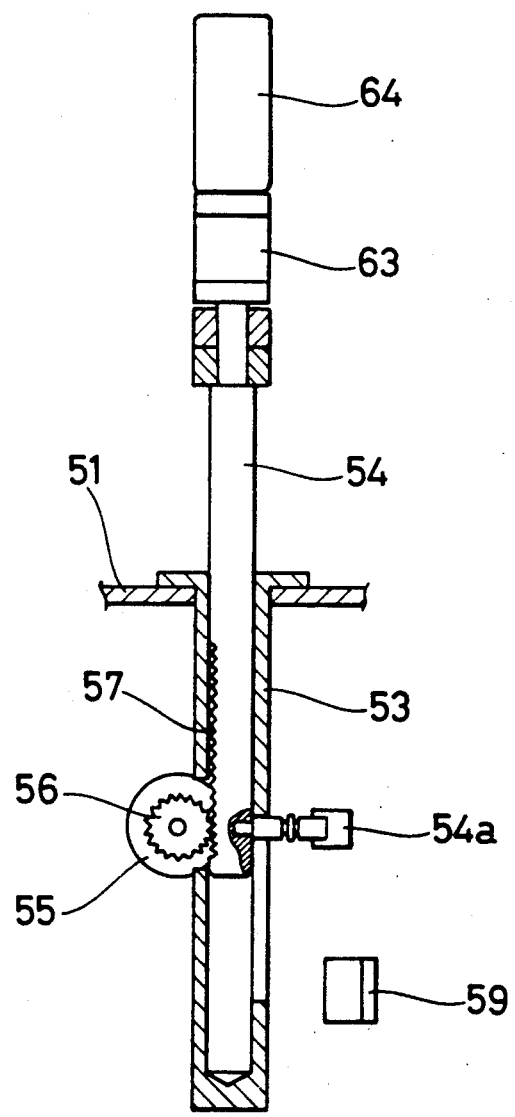

In FIGS. 6 to 8, the reference 50 denotes a probe operating unit which is provided with a casing 51 and a mount member 52 having a pipe 52a to be fitted the mount piece 8, the casing 51 accommodating therein linear and radial scan mechanisms. The pipe 52 of the mount member 52 is internally formed with a passage 52b for threading therethrough the insert member 2 of the ultrasound probe 1. In this embodiment, as will be described hereinlater, a manually operable rotating member is provided on the part of the casing 51, instead of on the connector 6' at the terminal end of the ultrasound probe 1 which is threaded through the passage 52b of the pipe 52.

The linear scan mechanism for the ultrasound probe 1 includes an operating rod 54 slidably fitted in an enclosure 53 which is fixedly provided in the casing 51. The operating rod 54 is provided with a rack 57 along its body for meshing engagement with a pinion 56 which is connected to an encoder 55. Similarly to the above-described first embodiment, the operating rod 54 is constantly urged outward under the influence of a return spring 58, and provided with a light blocking plate 54a at its inner end to detect the end position of its inward stroke in cooperation with an optical sensor 59.

Figure 9:
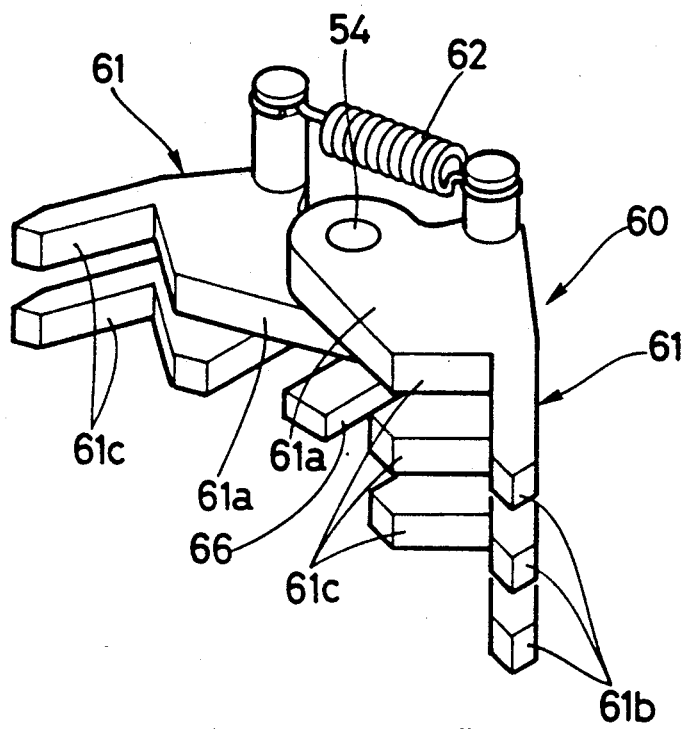
Figure 10:
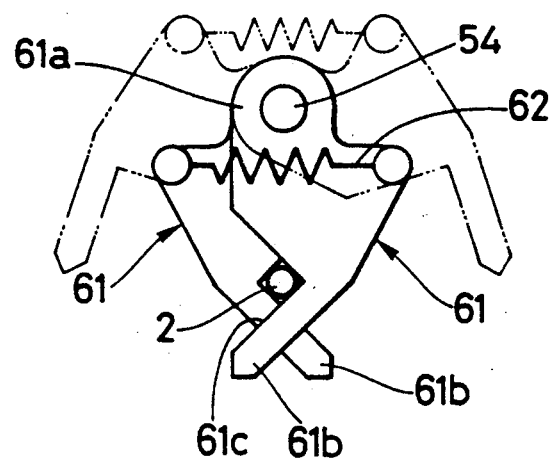

As seen in FIGS. 9 and 10, a probe gripper member 60 is contiguously extended from one side of the operating rod 54 to hold fixedly the insert member 2 of the ultrasound probe 1, the probe gripper member 60 having a pair of clamp members 61 which are each constituted by a rocking plate 61a pivotally fitted on the operating rod 54 and a plural number of gripping fingers 61b extending from the body of the clamp member 61 in parallelly spaced relation with each other in the axial direction of the operating rod 54. The width of the spacing between the adjacent gripping fingers 61b is greater than the thickness of the fingers so that, when the two clamp members 61 are turned toward each other, the gripping fingers 61b of one clamp member 61 snugly fit in the spacings between the gripping fingers 61b of the other clamp member 61 in an interlaced fashion. Each clamp member 61 is provided with a V-shaped notch on the inner side of each gripping finger 61b to provide gripping surfaces 61c. As the two clamp members 61 are turned toward each other, the insert member 2 which is located between the gripping fingers 61b of the two clamp members 61 is guided along the inclined gripping surfaces 61c and finally gripped between the bottoms of the V-shaped notches. In this gripped state, the respective gripping fingers 61b of the two clamp members 61 hold the insert member 2 in position with gripping forces which tend to deform the insert member 2 into a zigzag shape.

A clamping spring 62 is connected between spring bearing pins on the rocking plates 61a, urging the clamp members 61 toward each other or in the clamping direction toward the insert member 2. Normally, the clamping spring 62 acts to urge the gripping fingers 61b in the interlacing direction or toward the insert member 2. However, the clamping spring 62 has the so-called toggle function, acting to spread apart the gripping fingers 61b of the opposing clamp members 61 when the gripping fingers 61b are turned away from each other against the biasing force of the spring 62 beyond the most stretched point of the spring. Thus, the insert member 2 is securely embraced from both sides by the gripping surfaces of a plural number of interlaced fingers 61b of the two clamp members 61, irrespective of the diameter of the insert member 2. Indicated at 66 is a stopper member which restricts spontaneous rocking movement of the clamp members 61.

Figure 11:
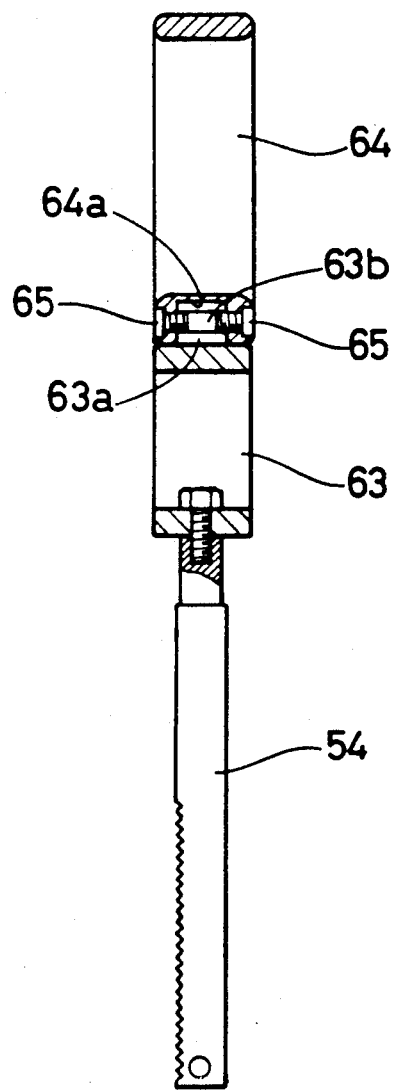
Figure 12:
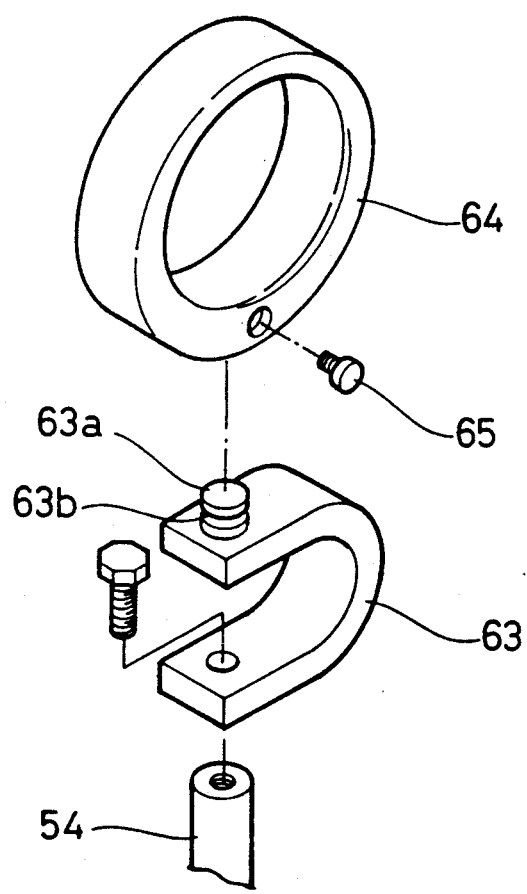

In this manner, the insert member 2 is operatively connected to the operating rod 54 which is manipulated by an operator's finger or fingers. For facilitating the manipulation of the operating rod 54, a finger ring 64 is attached to the outer end of the operating rod 54 through a connecting member 63. The finger ring 64 is in the form of an eccentric ring having an inner periphery which is formed eccentrically relative to its outer periphery. As seen in FIGS. 11 and 12, for attachment to the operating rod 54, the finger ring 64 is provided with a circular recess 64a on the outer side of its thick wall portion for fitting engagement with a projection 63a on the top side of the connecting member 63. The projection 63a is provided with an annular groove 63b around its circumference in the recess 64a to receive screws 65 which are threaded thereagainst from the opposite sides of the finger ring 64. Thus, the finger ring 64 is rotatably connected to the outer end of the operating rod 54 by the screws 65 which have a function of preventing the finger ring 64 from falling off.

Turning now to the radial scan mechanism, it includes an electric motor 70 which is provided within the casing 51 to rotationally drive, through a transmission gear means 71, a rotary member 72 with which the terminal connector 6' of the ultrasound probe 1 is coupled. Therefore, upon rotating the rotary member 72 by the motor 70, its rotation is transmitted to the connector 6' and to the ultrasound transducer 4 on the rigid tip member 3 which is connected to the connector 6' through the flexible transmission shaft 2b. In this instance, an encoder 73 is connected to the rotary member 72 to detect the rotational angle of the rotary member 72. This rotary member 72 is connected to a rotary part 75a of a rotary connector 75 through a joint 74. Fixed part 75b of the rotary connector 75 is securely fixed to a wall member 51 which is provided contiguously with the casing 51. On the other hand, the rotary member 72, joint 74 and rotary part 75a of the rotary connector 75 are rotatably supported in the casing 51 by bearings 76 and 77.

The rotary connector 75 has the same construction as the rotary connector 15 of the above-described first embodiment, and the ultrasound transducer 4 on the tip member 3 at the fore end of the ultrasound probe 1 is connected to the ultrasound image observation terminal T through substantially the same routes of electric connection as in the first embodiment, from the connector 6' to the rotary member 72 and then to the rotary connector 75 and a cable 78. However, in this case a manually operable rotating member 79 is provided integrally with the rotary member 72. The joint 74 which is inserted between the rotary member 72 and the rotary connector 75 facilitate electric wiring between these components, and can serve as means for supporting a baseboard of necessary electric circuit components.

The rotational axis A1 of the rotary member 72, joint 74 and rotary part 75a of the rotary connector 75 is not in parallel relation with the axis A2 of the operating rod 54 of the linear scan mechanism, and inclined through an angle $\theta$ in such a way as to get closer to the operating rod 54 on the inner side or on the side of the rotary connector 75 than on the outer side or on the side of the rotary member 72. With this arrangement, the insert member 2 between the probe gripper member 60 and the rotary member 72 can be looped smoothly in an arcuate shape free of bulging deformation at its gripped or connected portion.

The ultrasound probe operating mechanism of the invention further includes a mode selector mechanism for switching the operation between linear and radial scan modes. In this connection, even in case of a linear scan operation, the manual rotating member 79 which is provided integrally with the rotary member 72 is necessary to turn the ultrasound transducer accurately into a direction of interest. However, the rotating member 79 is knurled around its circumference, so that, from the standpoint of maneuverability in operation, it is preferred to be concealed under a cover in radial scan operations. For this purpose, a slidable cover member 80 is provided on the casing 51, the cover member 80 being located over the rotating member 79 to conceal same at the time of radial scan and being moved to a receded position to expose the rotating member 79 at the time of linear scan.

Figure 13:
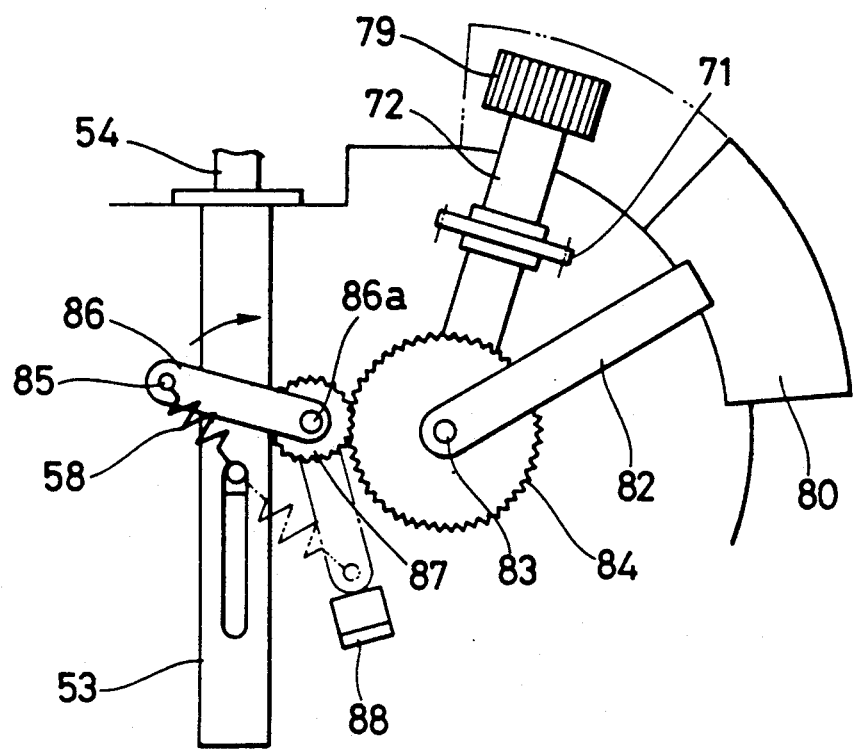
Figure 14:
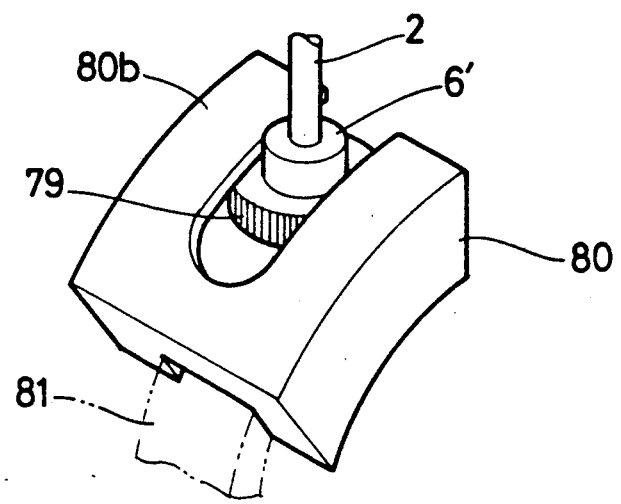

As clear from FIG. 13, the cover member 80 is provided with a side wall 80a substantially of U-shape in section to accommodate the rotating member 79 therein, and a top wall which is formed contiguously with the side wall 80a and provided with a U-shaped notch to receive the insert member 2 therein. The cover member 80 is mounted on the casing 51 slidably along a guide rail 81 which is provided along a curved top wall portion 51b of the casing 51, and connected to the outer end of a lever 82 the inner end of which is integrally connected to a rotational shaft 83. A gear 84 which is mounted on the rotational shaft 83 is meshed with a gear 87 on the rotational shaft 86a of a rocking plate 86 with a spring bearing for the return spring 58, which urges the operating rod 54 in the outwardly protruding direction. Accordingly, as the cover member 84 is located in the receded position indicated by solid line in FIG. 13, the rotating member 79 is exposed and can be operated with fingers, and the operating rod 54 is urged into the outwardly protruded position by the action of the return spring 58. It follows that the operating rod 54 is constantly urged to protrude its outer end portion out of the casing 51 in linear scan, ensuring smooth linear scan operations. Further, in radial scan, the cover member 80 is slided along the guide rail 81 to take the advanced position indicated in phantom in FIG. 13, concealing the rotating member 79 thereunder as shown in FIG. 14 and keeping same safely from the operator's fingers during a radial scan operation. Besides, in case the operating rod 54 is found to be located halfway of its stroke range prior to a radial scan operation, due to weakened biasing force of the return spring 58 acting on the operating rod 51, the operator can easily correct the position of the operating rod 51 by manipulating the finger ring 64.

Since the cover member 80 is located in different positions in the linear and radial scan operations, it can be used as a mode selector means. Namely, as the cover member 80 is slid into the covering position, its movement is followed by a rotational movement of the rocking plate 86 which is in turn detected by an optical sensor 88. When the rocking plate 86 is moved into a position which is detected by the optical sensor 88, the mode of operation is switched from the linear to radial scan mode.

Figure 15:
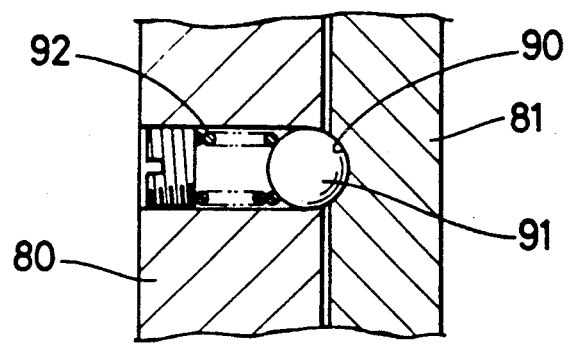

Further, in order to retain the cover member 80 stably in each of the covering position and the receded position, a groove 90 is provided on the part of the guide rail 81 as shown in FIG. 15, and a click ball 91 is provided on the side of the cover member 80, the click ball 91 being urged outward by a click spring 92 for fitting engagement with the groove 90 on the guide rail 81. By this click mechanism, the cover member 80 is correctly and stably retained in each of the advanced covering position and the receded position.

In use, the insert portion 3 of the endoscope S is introduced into a patient's body until its fore end reaches a locality of interest, and then the insert member 2 which has been placed in a biopsy channel C of the endoscope S is fed forward to protrude the tip member 3 from the fore end of the biopsy channel C over a predetermined length. On the other hand, the proximal end of the insert member 2, which has been threaded through the passage 52a in the mount member 52 on the operating unit 50, is connected to the rotary member 72 on the operating unit 50 in such a manner as to form an arcuate loop between the mount member 52 and the rotary member 72. Then, the paired clamp members 61 of the gripper mechanism 61 are closed to grip the insert member 2 at a position above the mount member 52. At this time, the gripping fingers 61b of the clamp members 61 are urged into the closed interlacing position by the clamp spring 62, which however has the toggle function as mentioned hereinbefore, acting to spread apart the clamp members 61 when they are turned away from each other beyond a certain point. Therefore, the clamp members 61 can be retained in an open state, spread apart from each other by a predetermined angle. In this state, the insert member 2 is placed between the opposing gripping fingers 61b, and then at least one of the clamp members 61 is turned toward the other one, whereupon the two clamp members 61 are turned toward each other by the action of the clamp spring 62 to hold the insert member 2 in the interlaced gripping fingers 61b, thus operatively connecting the insert member 2 to the operating rod 54.

Now, in order to perform a linear scan operation, the cover member 80 is pushed into the receded position, for example, with a finger. By so doing, the scan mode is automatically switched into the linear scan mode. The operating rod 54 is then pushed into the casing 51 by manipulating the finger ring 64 as far as the end position of its inward stroke where the light blocking plate 54a at the inner end of the operating rod 54 is detected by the optical sensor 62, thereby protruding the tip member 3 of the ultrasound probe 1 from the biopsy channel C over a predetermined length. Thereafter, the pushing force on the operating rod 54 is removed to permit the rod 54 to move outward or in the protruding direction under the influence of the return spring 58. This outward stroke of the operating rod 54 is accompanied by transmission of ultrasound pulses and reception return echoes to make a linear scan examination. At this time, the ultrasound transducer 4 can be adjusted into a desired direction, since the cover member 80 is in the receded position to expose the rotating member 79 in an easily accessible state for manipulation by the operator. Consequently, the ultrasound transducer 4 on the rigid tip member 3 can be oriented correctly, for example, to face an intracavitary wall portion to be examined.

For a radial scan, the cover member 80 is pushed into the receded position, thereby turning the rocking plate 86 through a predetermined angle. This angular movement of the rocking plate 86 is detected by the optical sensor 88 to switch the operation to the radial scan mode, whereupon the motor 70 is actuated to rotate the rotary member 72 through the transmission gear means 71. As a consequence, the rotation of the rotary member is transmitted to the connector 6 which is coupled with the rotary member 7 and to the flexible rotation transmitting shaft 2b which is fixed to the connector 6, thereby turning the tip member 3 together with the ultrasound transducer 4 for a radial scan. The angular displacement of the rocking plate 86 weakens the force of the return spring 58 over the entire stroke range of the operating rod 54, which is advantageous to the adjustment of the radial scan position. Besides, the rotating member 79, which is put in rotation at a predetermined speed during the radial scan, is concealed under the cover member 80, precluding the possibilities of the rotating member 79 being touched by the operator's finger or hand.

Figure 16:
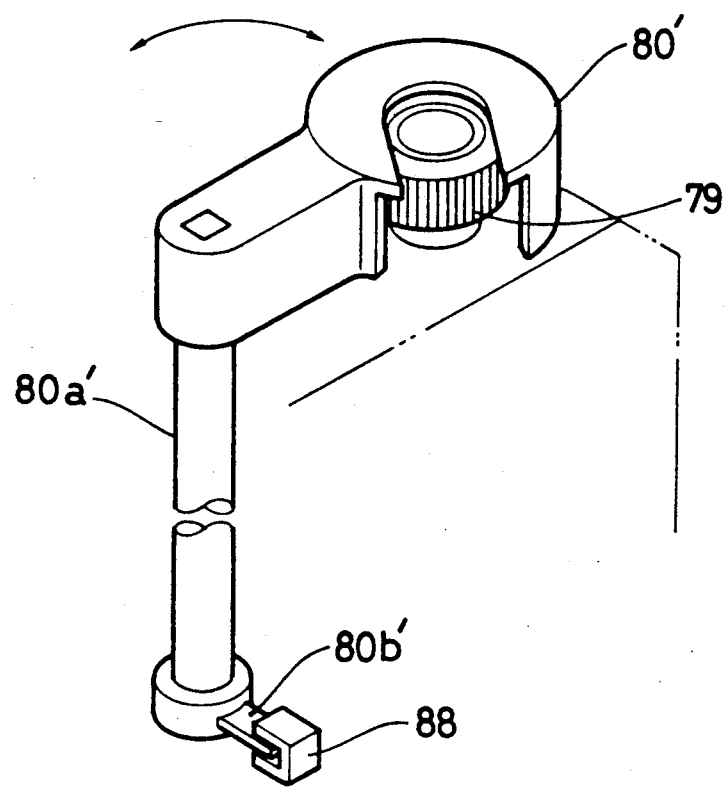
FIG. 16 is a schematic perspective view of a cover member and a scan mode selector mechanism in a third embodiment of the invention.

With regard to the function of switching the scan mode by way of the shift of position of the cover member 80 in the above-described second embodiment, if there is no necessity for weakening the force of the return spring 58 in the radial scan mode, there may be employed an arrangement as shown in FIG. 16, mounting a cover member 80' on a shaft 80a' for rocking movement in the arrowed directions and providing a light blocking plate 80b' at the tip end of the shaft 80a such that the light blocking plate 80b' is brought to a position to be detected by an optical sensor 88' when turned about its axis together with a switching movement of the cover member 80'.

What is claimed is:

1. An ultrasound internal examination system, comprising:
    an ultrasound probe having an ultrasound transducer rotatably mounted on a tip end portion of a flexible insert member, said flexible insert member having a rotation transmitting means connected to said tip end portion for transmitting rotation to said ultrasound transducer, and a flexible sleeve fitted around said rotation transmitting means, said rotation transmitting means relatively rotatable to said flexible sleeve;
    a probe operating unit detachably connected to a base end portion of said flexible insert member including a linear operating means for moving said ultrasound transducer linearly along a longitudinal axis of said tip end portion for linear scanning, and a radial operating means to turn said ultrasound transducer about the longitudinal axis of said tip end portion for radial scanning;
    said linear operating means having an operating rod reciprocally mounted through a casing of said probe operating unit and detachably connected to said flexible sleeve and movable into and out of said casing for linear scanning by said ultrasound transducer, and a position sensor means for detecting a position of said ultrasound transducer by detecting a displacement of said operating rod;
    said radial operating means having a rotary member coupled with said rotation transmitting means, a motor for rotatably driving said rotary member, a rotation sensor means for detecting a rotational angle of said rotary member, and a rotary connector for connecting rotatable signal lines from said ultrasound transducer to a static part of said operating unit; and
    a scan mode selector means for switching an operation of said ultrasound transducer between a linear scan mode and a radial scan mode.

2. An ultrasound examination system as defined in claim 1, wherein said scan mode selector means is a switch means mounted on said probe operating unit.

3. An ultrasound examination system as defined in claim 1, further comprising:
    a manually operable rotating member provided on said probe operating unit to turn said ultrasound transducer by a manual operation;
    a cover member provided on said operating unit movable to a covering position to conceal said rotating member thereunder during said radial scan mode; and
    a switch means for automatically switching operation of said probe to said radial scan mode when said cover member is moved into said covering position.

4. An ultrasound examinations system as defined in claim 1, wherein said radial operating means includes a rotational mechanism having an axis of rotation inclined inwardly toward a longitudinal axis of said operation rod of said linear operating means.

5. An ultrasound examination system as defined in claim 1, wherein said rotary connector includes electrically conductive fluid electrically connecting said rotatable signal lines to said static part of said operating unit.

6. An ultrasonic examination system, comprising:
    an ultrasonic probe having an ultrasonic transducer mounted on a tip end portion of a flexible insert member which is surrounded by a flexible sleeve;
    a probe operating unit surrounded by a casing and connected to a base end portion of said flexible insert member, including a linear operating means for moving said ultrasonic transducer linearly along a longitudinal axis of said tip end portion for linear scanning operations, and a radial operating means to rotate said flexible insert member and said ultrasonic probe about the longitudinal axis of said tip end portion for radial scanning operations;
    said linear operating means having an operating rod reciprocally mounted to said casing of said probe operating unit to linearly move said ultrasonic transducer, and a position sensor means for detecting a position of said ultrasound transducer by detecting a displacement of said operating rod;
    said radial operating means having a motor for rotatably driving said flexible insert member, a rotation sensor means for detecting a rotational angle of said flexible insert, and a rotary connector for connecting rotatable signal lines from said ultrasound transducer to a static part of said operating unit; and
    a scan mode selector means for switching an operation of said ultrasonic transducer between a linear scan mode and a radial scan mode.

7. An ultrasound examination system as defined in claim 6, wherein said scan mode selector means is a switch mounted on said probe operating unit.

8. An ultrasound examination system as defined in claim 6, further comprising:
    a manually operable rotating member provided on said probe operating unit to turn said ultrasound transducer by a manual operation;
    a cover member provided on said operating unit movable to a covering position to conceal said rotating member thereunder during said radial scan mode; and
    a switch means for automatically switching operation of said probe to said radial scan mode when said cover member is moved into said covering position.

9. An ultrasound examinations system as defined in claim 6, wherein said radial operating means includes a rotational mechanism having an axis of rotation inclined inwardly toward a longitudinal axis of said operation rod of said linear operating means.

10. An ultrasound examination system as defined in claim 6, wherein said rotary connector includes electrically conductive fluid electrically connecting said rotatable signal lines to said static part of said operating unit.

* * * * *